United States Patent
Perkins

Patent Number: 6,159,255
Date of Patent: *Dec. 12, 2000

[54] METHOD FOR PREDICTING INTRINSIC PROPERTIES OF A MIXTURE

[75] Inventor: Jonathan H. Perkins, Wenonah, N.J.

[73] Assignee: Sunoco, Inc. (R&M), Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 09/209,803

[22] Filed: Dec. 11, 1998

[51] Int. Cl.[7] .................. C10L 1/06; G01J 3/42; G01N 33/22

[52] U.S. Cl. .............. 44/300; 250/339.07; 250/339.12; 585/14; 700/268; 702/30

[58] Field of Search ............... 585/14; 44/300; 700/268; 702/30

[56] References Cited

U.S. PATENT DOCUMENTS

| | | | |
|---|---|---|---|
| 4,677,567 | 6/1987 | Grosser et al. | 364/502 |
| 4,963,745 | 10/1990 | Maggard | 250/343 |
| 5,121,337 | 6/1992 | Brown | 364/498 |
| 5,225,679 | 7/1993 | Clarke et al. | 250/343 |
| 5,349,188 | 9/1994 | Maggard | 250/339 |
| 5,397,899 | 3/1995 | DiFoggio et al. | 250/339.09 |
| 5,412,581 | 5/1995 | Tackett | 364/498 |
| 5,452,232 | 9/1995 | Espinosa et al. | 364/498 |
| 5,475,612 | 12/1995 | Espinosa et al. | 364/500 |
| 5,504,331 | 4/1996 | Lane et al. | 250/339.09 |
| 5,512,751 | 4/1996 | Murray, Jr. et al. | 250/339.09 |
| 5,668,374 | 9/1997 | DiFoggio et al. | 250/339.12 |
| 5,712,481 | 1/1998 | Welch et al. | 250/339.12 |
| 5,763,883 | 6/1998 | Descales et al. | 250/339.09 |
| 5,861,228 | 1/1999 | Descales et al. | 436/171 |
| 6,070,128 | 5/2000 | Descales et al. | 702/30 |

OTHER PUBLICATIONS

Morris, William E., "Optimum blending gives best pool octane", *Oil & Gas Journal*, Jan. 20, 1986, pp. 63–66.

*Primary Examiner*—Ellen M. McAvoy
*Attorney, Agent, or Firm*—Kenneth Crimaldi; Robert A. Koons, Jr.; Pepper Hamilton LLP

[57] ABSTRACT

A method for predicting an intrinsic property of a mixture comprising at least two components by: (a) selecting components and an equation; wherein the equation relates amounts of the components to the intrinsic property of the mixture; (b) selecting experimental compositions, each of which comprises at least one of the components; (c) measuring a correlational property of each of the experimental compositions by a correlational technique; and (d) determining a set of coefficients for the equation; wherein in the equation, each of the coefficients is multiplied by a concentration of a component or a product of concentrations of two or more components.

16 Claims, 2 Drawing Sheets

METHOD FOR PREDICTING INTRINSIC PROPERTIES OF A MIXTURE

BACKGROUND OF THE INVENTION

1. Field of the Invention

This invention relates to a method for predicting an intrinsic property of a mixture comprising at least two components.

2. Background of the Invention

Gasoline blending is a complex process whose goal is a gasoline blend that meets a variety of environmental and contractual specifications, and has the lowest possible cost. Typically, from five to fifteen blend stocks are available for blending. Some of the components will have a high economic value because they meet many of the specifications and are difficult to produce, e.g., alkylate stocks. Others will have a low economic value because they do not meet specifications, but are relatively easy to produce. The availability and properties of the blend stocks vary with changes in refinery operation.

In order to accomplish this goal, it is desirable to have an accurate model to predict gasoline properties from the amounts and properties of the component blend stocks. If the model is inaccurate, one or more properties of the blended gasoline will differ from the prediction, and the blended gasoline may not meet specifications. In such a case, blending needs to be performed with a process control system which adjusts the amounts of the components during blending, or in some cases, the gasoline will need to be reblended with high-value components. Use of an accurate model could avoid these inefficiencies and might save millions of dollars over the course of a year.

The simplest type of blend model is the linear model, which has the following form:

$$y = \sum_{i=1}^{m} b_i c_i$$

where y is the property of the blend, m is the number of components in the blend, $c_i$ is the volume fraction of the $i^{th}$ component and $b_i$ is the model coefficient for the $i^{th}$ component. The coefficients are sometimes referred to as the neat values because if the blend recipe is simply a pure component, i.e., $c_i=1$ and all other c's are 0, then the predicted property is equal to the coefficient for the component. The linear model assumes that the blend property is a flat surface between the values of the pure compounds. This will be true in an ideal system having no interactions between the components. To the extent that this assumption is incorrect there is a difference between the true property and the prediction of the linear model. An example of a linear blend model is described in U.S. Pat. No. 5,475,612 to Espinosa. Properties for a blend of hydrocarbon components are predicted using a linear equation. Each term in the equation is the product of a quantity derived from a near-infrared spectroscopy (NIR) measurement of a component and the volume fraction of that component. The NIR measurements are performed only on single components, with no data obtained from mixtures of components. In addition, no interaction terms are used in the blend model equation. This method cannot account for non-additive effects on mixture properties caused by interactions between components.

An approach to modeling blend systems in which there is a significant interaction between the components is the interaction model. A binary interaction model includes terms which account for pair-wise interactions between components, and has the following form:

$$y = \sum_{i=1}^{m} b_i c_i + \sum_{i=1}^{m-1} \sum_{j=i+1}^{m} b_{ij} c_i c_j$$

The first term in this equation is equivalent to the linear model and the second term is a non-linear term to account for the curvature present in the actual property surface. The $b_i$ coefficients are the linear terms and the $b_{ij}$ coefficients are the binary interaction terms. Higher-order interaction terms which comprise a coefficient and the product of three or more concentrations can be added to the model, but are typically not significant.

Use of the binary interaction model to predict octane values in blended gasoline is described in W. E. Morris, Oil & Gas Journal, Jan. 20, 1986. Morris suggests that all coefficients be determined by actual measurements of pure components or blends. The linear $b_i$ coefficients are then automatically equal to the property of the pure $i^{th}$ component. Morris determines of the interaction coefficients by measuring octane values for a 50:50 blend of each pair of components in addition to the pure components.

Application of the method suggested by Morris requires determination of a large number of property values, which may need to be repeated as the composition of blend components changes. For example, application of the interaction model to predict octane number for a mixture often gasoline feed stocks requires analysis of 55 samples in a knock engine, a time-consuming procedure. Alternatively, libraries of octane interaction values are available in the literature. An obvious problem with using literature values is that a particular blending stock may be very different, depending on location and time of production.

Another problem with actual property measurements on neat components and 50:50 blends is that the neat and 50:50 blend samples used to determine the interaction coefficients are extreme samples. There are no practical gasoline blends with compositions that are close to these values. Thus, coefficients derived from such samples will not reliably predict properties of actual gasoline blends. Another consequence of the extreme nature of these samples is that accurate measurement of some properties, e.g., octane values, will not be possible for some components and mixtures having large amounts of components with high vapor pressures, e.g., butane and light cracked gas.

Actual property measurements on more realistic samples tend to be inaccurate due to errors in volume measurement of components present at low concentrations. Such errors are exacerbated because the difficulty of performing actual property measurements leads to measurement of only a small number of samples, which does not allow averaging of errors.

SUMMARY OF THE INVENTION

This invention is directed to a method for predicting an intrinsic property of a mixture comprising at least two components by: (a) selecting components and an equation; wherein the equation relates amounts of the components to the intrinsic property of the mixture; (b) selecting experimental compositions, each of which comprises at least one of the components; (c) determining a correlational property of each of the experimental compositions by a correlational technique; and (d) determining a set of coefficients for the equation; wherein in the equation, each of the coefficients is multiplied by a concentration of a component or a product of concentrations of at least two components.

DETAILED DESCRIPTION OF THE INVENTION

Figure 1:
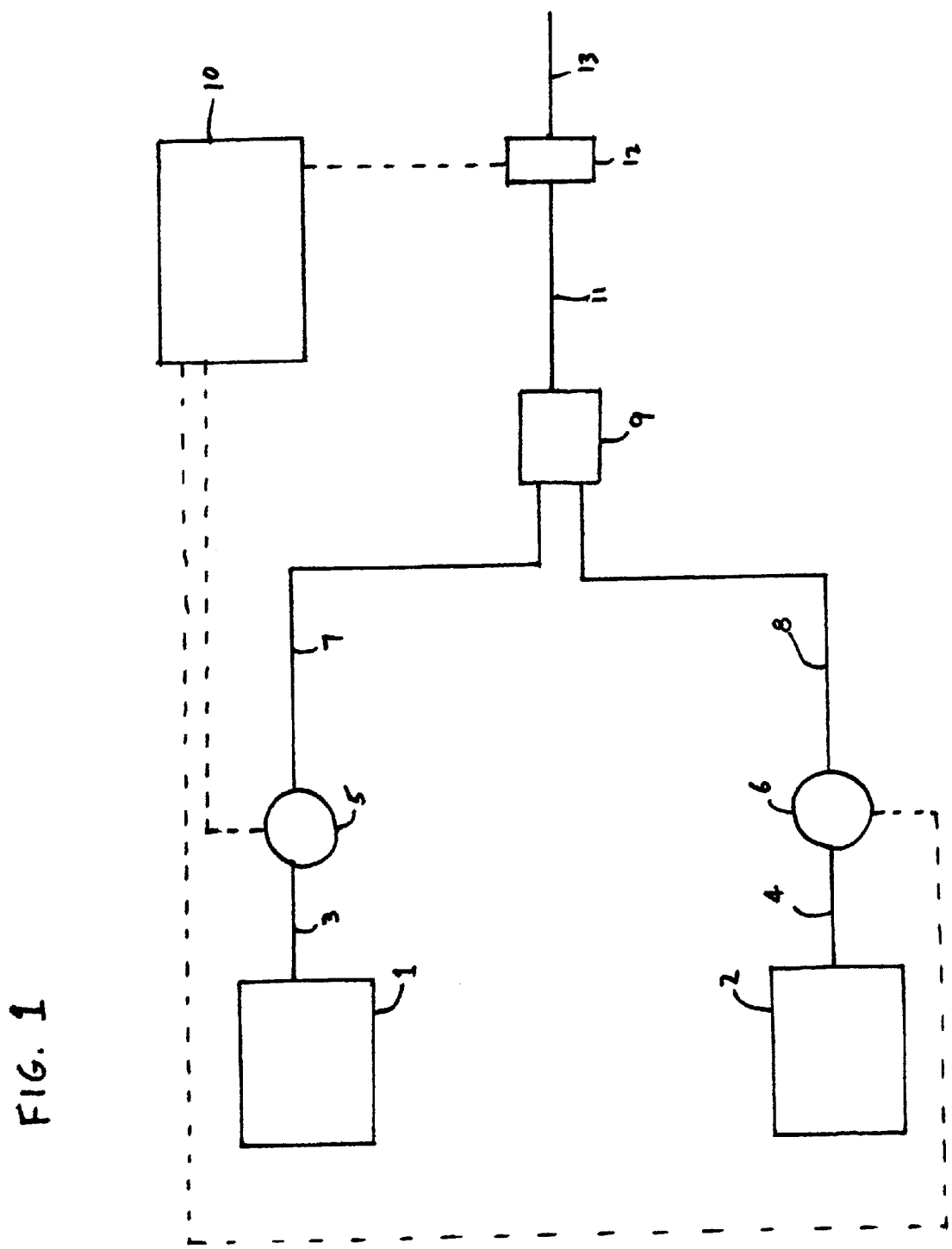
FIG. 1 is a schematic diagram of an apparatus for producing mixtures of two components and performing NIR measurements on the mixtures.

In the method of this invention, coefficients are obtained for use in an equation relating an intrinsic property of a mixture to the concentrations of its components. These coefficients are calculated from data obtained by measuring a property of each of a group of experimental compositions using a correlational technique. Each experimental composition comprises either a single component or a mixture of two or more components. The property data obtained from the experimental compositions are mathematically correlated by known methods with the intrinsic property of the experimental compositions, thereby producing a set of mathematically determined correlational properties. These correlational properties are then used to determine a statistically significant set of coefficients for that particular intrinsic property.

It is preferred that the equation has the form of an interaction model, and most preferred that it has the form of a binary interaction model. A set of equation coefficients is generated for each intrinsic property of interest. The advantage of deriving the coefficients from data obtained by means of a correlational technique is that correlational techniques are typically much faster and easier to use than actual direct measurements of the intrinsic property of interest. Any multivariate technique may be used as a correlational technique. The preferred correlational techniques are the spectroscopic techniques, including infrared spectroscopy (IR), near-infrared spectroscopy (NIR), nuclear magnetic resonance spectroscopy (NMR), ultraviolet spectroscopy (UV) and Raman spectroscopy. In each of these techniques, the property being measured is an absorbance or group of absorbances. The absorbance or group of absorbances is mathematically correlated with the intrinsic property of the experimental composition to produce the correlational property. The most preferred correlational technique for organic compounds is NIR. NIR spectra measure the intensity of the overtones of the carbon-hydrogen, oxygen-hydrogen and nitrogen-hydrogen absorption bands. The carbon-hydrogen (C—H) absorption bands are typically the most useful for mixtures of organic compounds. Different types of C—H bonds, e.g., aromatic, aliphatic and olefinic, absorb light at different characteristic frequencies. The magnitude of the absorption band is proportional to the amounts of the C—H bonds in the sample. Therefore the NIR spectrum is a fingerprint of the sample composition. This fingerprint can be empirically related to the intrinsic properties of the sample.

The term "component" as used herein refers to either a mixture of compounds or a substantially pure compound. Although the method of this invention is broadly applicable to mixtures produced from any number of components, it is most useful where there are from five to twenty components. It is most preferred that there are from six to twelve components.

In a preferred embodiment of this invention in which the mixture is a gasoline blend, intrinsic properties of the sample which are of particular interest include research octane number (RON), motor octane number (MON), pump octane ((R+M)/2), distillation temperatures (in °F.) at which a given volume percentage of the sample is distilled (T10, T50, T90), the volume percentage of the sample evaporated at a given temperature in °F. (E200, E300), %Aromatics, %methyl-tert-butyl ether (%MTBE), %Benzene, Reid vapor pressure (RVP), V/L and specific gravity. However, NIR cannot be used to determine the sulfur content of gasolines or any octane number for leaded gasolines.

The property measured for each of the experimental compositions is correlated with the intrinsic property of interest using a correlational model. This correlational model is developed by a separate process involving the following steps: 1) calibration samples covering a wide range of realistic compositions are collected; 2) a multivariate property, e.g., NIR absorptions, of each sample is measured using a correlational technique; 3) the intrinsic property, e.g., the octane number, of the sample is measured; 4) an empirical model linking the multivariate property to the intrinsic property is developed using a chemometric method; and 5) the performance and significance of the model is tested using new samples. Correlational models for a variety of techniques are available. The models can be generated using a wide variety of chemometric techniques, including multiple linear regression (MLR), principal component regression (PCR), partial least squares (PLS) and artificial neural nets (ANN). The models can be linear or non-linear. Examples of correlational models used on data from spectroscopic methods include those provided with spectrophotometers sold by Orbital Sciences Corp. (Pomona, Calif.) for RON, MON, RVP, cetane, %oxygenates, %olefins, %aromatics and distillation points; UOP Guided Wave (El Dorado Hills, Calif.) for %aromatics, %alcohols, color, distillation points, cloud points, RON, MON, (R+M)/2, RVP, %benzene, PONA (paraffins, olefins, naphthenes, aromatics); Applied Automation (Bartlesville, Okla.) for RON and MON; and Varlen Instruments (Bellwood, Ill.) (PETROSPEC) for %MTBE, %benzene, %olefins, %aromatics, %saturates, RON, MON, (R+M)/2, distillation points, and evaporation points.

The experimental compositions are mixed manually by volume, manually by weight, manually by weight with conversion to volume using known or measured densities, or automatically by volumetric pumps or automated balances. Automated preparation and measurement of liquid experimental compositions can be performed in a computer-controlled system in which various combinations of a set of liquid components are mixed and analyzed by a spectrophotometer according to a predetermined scheme. For example, the simplest form of such an apparatus is depicted in FIG. 1; it allows automated mixing of two components in a variety of predetermined amounts, with analysis of each mixture by a NIR spectrophotometer. The components are placed in reservoirs 1 and 2, e.g., storage tanks or bottles, that are connected by lines 3 and 4 to high-precision pumps 5 and 6, respectively. Each component is typically a mixture of compounds, but in some cases, a component may be a substantially pure compound. The computer controls the pumps such that flow is allowed through lines 7 and 8 at rates that assure the correct proportions of the components in the experimental composition are achieved in the mixing chamber 9. In another embodiment of the invention in which automatic valves are used in place of the pumps, an upstream source of pressure is provided to force the liquid components through those valves that have been opened by the computer. Prior to each time that the computer 10 collects and analyzes a NIR spectrum, an adequate amount of the experimental composition is passed through line 11 and the NIR cell 12 to thoroughly rinse the cell through line 13 into a waste or storage container so that the compositions of the mixture in the mixing chamber and that in the NIR cell are substantially identical. The computer then starts the next experimental composition by changing the settings of the pumps. When the required experimental compositions have all been analyzed, the computer has all of the necessary information to calculate interaction model coefficients.

It will be apparent that additional reservoirs and additional pumps or valves with their associated lines may be added to the apparatus shown in FIG. 1. This will result in an apparatus capable of mixing various experimental compositions, each containing at least two components selected from a much larger number of components, and analyzing mixtures derived therefrom. It is contemplated that the apparatus can be configured with sufficient reservoirs, lines and pumps or valves to mix as many as 20 components. Preferably, there are at least five components, and more preferably, there are from six to twelve components. Analysis of the experimental compositions can be performed using spectrophotometric methods other than NIR, e.g., IR, NMR, UV and Raman spectroscopy.

It is preferred that the computer also use the coefficients obtained from analysis of the experimental compositions to calculate the optimum proportions of the components that will produce the most economical mixture having a desired set of properties. It is then possible for the computer to automatically mix the calculated proportions of components to verify that the mixture has the desired properties. In one embodiment of the invention, the computer has a predetermined experimental design that is followed regardless of the results obtained in any particular analysis. In another embodiment, the computer is set to run in an interactive or adaptive mode in which the results of the analysis of some of the experimental compositions guide the creation of the next set of experimental compositions. An example of this type of operation is an iterative optimization in which the computer creates and analyzes mixtures using an optimization algorithm, e.g., the simplex method, as described by S. N. Deming & S. L. Morgan, Analytical Chemistry, 45:278A (1973), to find proportions that produce a mixture meeting a set of specifications and having the minimum cost. In this iterative optimization, no equation or coefficients are required or determined because the method entails a simple empirical optimization which produces directly a set of concentrations for the components.

The blend model coefficients are typically determined from the compositions of the experimental compositions and their correlational properties using the techniques of linear algebra. The following is an illustration of the use of linear algebra for an m-component mixture for which n samples are measured. X is an n by m matrix in which each row corresponds to an experimental sample and each column corresponds to a component. $X_{ij}$ is the volume percent of the $j^{th}$ component in the $i^{th}$ sample. X is augmented with the "interaction" columns. A binary interaction column is the element-wise product of two of the original linear columns. For example, if $$X = \begin{bmatrix} 0.3 & 0.7 \\ 0.5 & 0.5 \\ 0.1 & 0.9 \end{bmatrix}$$

then the augmented X would be $$X = \begin{bmatrix} 0.3 & 0.7 & 0.21 \\ 0.5 & 0.5 & 0.25 \\ 0.1 & 0.9 & 0.09 \end{bmatrix}$$

The model can be expressed according to linear algebra as $$Xb = y + e$$

where X is the augmented design matrix, b is the set of model coefficients expressed as a column vector, y is the set of measurements of the property derived from a fundamental property measured by the correlational technique and e is the set of residual errors of the interaction model. The model coefficients can be estimated by $$b = (X'X)^{-1}X'y$$

where the apostrophe indicates a transposed matrix. If the experiment is designed well then the X'X matrix is well conditioned and calculation of its inverse is stable. The elements in b are the linear and interaction coefficients that are used in the blending interaction model.

The robustness or statistical significance of the determined coefficients is dependent on many factors, but the two primary considerations are the precision of the measurement of the property, y, and the quality of the experimental design, i.e., the orthogonality of the columns in X and the number of samples. Correlational techniques are typically very precise compared to most reference techniques. This is especially true in the case where the mixture is a gasoline blend and the reference technique is measurement of octane in a knock engine. Even so, an experiment may not have sufficient power to provide statistical significance at a given confidence level, e.g., 95%, for the entire set of coefficients. Under these circumstances, the best subset of coefficients that are statistically significant is determined.

The following algorithm is a preferred method for determining the best subset of terms for the blending model. Other techniques will produce similar results depending on the starting assumptions. This algorithm assumes that the linear portion of the model is significant and determines the linear portion prior to adding interaction terms. Each interaction term is added in turn and tested independently. The interaction terms that explain the maximum amount of the variance are selected and if they pass the significance test, they are retained. Thus, the final equation does not necessarily include an interaction term for each pair of components.

I. Determine the linear portion of the model
  1) Define the following terms:
    X=n by m matrix of volume percentages of m components in n samples
    y=n by 1 vector of property values determined by correlational method
    b=m by 1 vector of linear coefficients to be determined
  2) Determine the coefficients $$b = (X'X)^{-1}X'y$$

3) Determine the F statistic for the model
a) determine estimated y values $$\hat{y} = Xb$$

b) determine the sums of squares (SS)

$$SS_{total} = \Sigma(y - \bar{y})^2$$

$$SS_{explained} = \Sigma(\hat{y} - \bar{y})^2$$

$$SS_{unexplained} = \Sigma(y - \hat{y})^2$$

c) determine the degrees of freedom (DOF)

$$DOF_{total} = n - 1$$

$$DOF_{explained} = m - 1$$

$$DOF_{unexplained} = n - m$$

d) determine the F ratio $$F = \frac{(SS_{explained} / DOF_{explained})}{(SS_{unexplained} / DOF_{unexplained})}$$

4) If the F statistic for the model passes the significance test then proceed to section II, otherwise re-evaluate the experimental design and start over.

II. Augment the model with the best interaction term

1) For each possible interaction term (interaction between components i and j where j>i):
   a) create a test X matrix from the X matrix and the interaction column $$X_{test} = [X \ X_{columni} * X_{columnj}]$$

b) recalculate the model $$b_{test} = (X'_{test} X_{test})^{-1} X'_{test} y$$

c) determine estimated y values $$\hat{y}_{test} = X_{test} b_{test}$$

d) determine the explained sum of squares $$SS_{explained} = \Sigma(\hat{y}_{test} - \bar{y})^2$$

2) Select the interaction term with the largest $SS_{explained}$
3) Determine the F statistic for the added interaction term
a) determine the sums of squares of the model without the added term $$b = (X'X)^{-1} X'y$$

$$\hat{y} = Xb$$

$$SS_{explained(without)} = \Sigma(\hat{y} - \bar{y})^2$$

$$DOR_{explained(without)} = m - 1$$

$$SS_{unexplained(without)} = \Sigma(y - \hat{y})^2$$

$$DOF_{unexplained(without)} = n - m$$

b) determine the sums of squares of the model with the added term $$b_{test} = (X'_{test} X_{test})^{-1} X'_{test} y$$

$$\hat{y}_{test} = X_{test} b_{test}$$

$$SS_{explained(with)} = \Sigma(\hat{y}_{test} - \bar{y})^2$$

$$DOF_{explained(with)} = m$$

$$SS_{unexplained(with)} = \Sigma(y - \hat{y}_{test})^2$$

$$DOF_{unexplained(with)} = n - m - 1$$

c) determine the sum of squares attributed to the added term $$SS_{difference} = SS_{explained(with)} - SS_{explained(without)}$$

$$DOF_{difference} = 1$$

d) determine the F ratio $$F = \frac{(SS_{difference} / DOF_{difference})}{(SS_{unexplained(with)} / DOF_{unexplained(with)})}$$

4) If the F ratio exceeds the 95% confidence limit then accept this new added term
   a) $X = X_{test}$
   b) $m = m + 1$
   c) because this interaction term has been used, remove it from the list of possible terms for future selection.
   d) repeat section II of this algorithm 5) If the F ratio does not exceed the 95% confidence limit then do not add this new term to the model and exit the algorithm.

Typically, when the coefficients have been determined for the final equation relating an intrinsic property to concentrations of components, the equation is used to predict the most economical set of concentrations of the components which will give a desired set of intrinsic properties when the components are blended at those concentrations. Commercially available software is used to calculate the component concentrations. For example, blending/planning software is available under the name PIMS from Aspentech (Cambridge, Mass.), MIMI from Chesapeake Decision Sciences (New Providence, N.J.) and GRTMPS-II from Haverly (Denville, N.J.). Typically, when an economically viable set of volume percentages is obtained from the final equation, the components are actually blended at these levels on a commercial scale to produce a mixture having the desired properties.

In a preferred embodiment of this invention in which the mixture is a gasoline blend, preferred models are those that accurately relate NIR spectra to intrinsic properties of gasoline components or mixtures thereof. Typically, when a NIR model is created from a set of calibration samples, a certain range of applicability is defined by the nature of the calibration samples. Spectra outside this range typically will not produce accurate predictions of properties. For example, if a gasoline octane model is created using only regular grade gasoline samples (pump octane number about 87), then this model will probably not be accurate for measuring octane on a premium grade gasoline. Moreover, the calibration samples used for NIR octane number models include only realistic gasoline compositions. Consequently, these models tend to be inaccurate for extreme gasoline compositions such as neat blend stocks and 50:50 blends, making them difficult to use in traditional interaction blending models that use pure component properties as the linear terms. However, the method of this invention calculates the linear terms for an octane number model from NIR-derived octane numbers, which are accurate over the range of realistic compositions. As a result, the octane number model derived according to this invention may not be accurate for neat blend stocks, but this is of no importance in predicting properties of actual gasoline blends.

The following Example is presented in order to illustrate various aspects of the present invention, but is not intended to limit the invention.

EXAMPLE

Coefficients were calculated from NIR data for determination of RON, MON, MTBE, Aromatics, Olefins, Saturates, Gravity, T10, T50, T90, V/L, RVP and Benzene for a gasoline blend containing nine components. The components were: Raffinate, Naphtha, CatGas, Alkylate, Reformate, MTBE, Light Straight Run (LSR), LtCat and Butane.

These experimental compositions were analyzed in a PIONIR 1024 NIR spectrophotometer (Orbital Sciences Corp.) calibrated to predict the properties listed above. The samples were analyzed by rinsing and filling the cell with sample, waiting 30 seconds for the temperature control to equilibrate, and then running the spectrophotometer. NIR property results were recorded directly to a file. These property results and the composition data were imported into a program written in MATLAB "language" (based on MATLAB software from The MathWorks, Inc., Natick, Mass.) to determine the linear and binary interaction coefficients according to the linear algebra methods discussed above. The program started with the nine linear terms and tested interaction terms for significance with an F test. Each interaction term was retained if the F test passed the 95% confidence limit. When the F test failed to meet this test, no additional interaction terms were evaluated.

The results for each of the selected properties are tabulated below. The first two columns indicate the component

TABLE 1

Experimental Compositions (target volume %)

|    | LSR | LtCat | Raffinate | Naphtha | CatGas | Alkylate | Reformate | Butane | MTBE |
|----|-----|-------|-----------|---------|--------|----------|-----------|--------|------|
| 1  | 8   | 8     | 8         | 8       | 25     | 18       | 14        | 7      | 4    |
| 2  | 30  | 8     | 8         | 8       | 12     | 12       | 10        | 8      | 5    |
| 3  | 8   | 30    | 8         | 8       | 12     | 12       | 10        | 8      | 5    |
| 4  | 8   | 8     | 30        | 8       | 12     | 12       | 10        | 8      | 5    |
| 5  | 8   | 8     | 8         | 30      | 12     | 12       | 10        | 8      | 5    |
| 6  | 1   | 1     | 1         | 1       | 90     | 2        | 2         | 1      | 1    |
| 7  | 4   | 4     | 4         | 4       | 6      | 66       | 5         | 4      | 3    |
| 8  | 6   | 6     | 6         | 6       | 9      | 9        | 49        | 6      | 4    |
| 9  | 8   | 8     | 8         | 8       | 13     | 13       | 11        | 25     | 6    |
| 10 | 9   | 9     | 9         | 9       | 14     | 14       | 12        | 9      | 16   |
| 11 | 29  | 29    | 5         | 5       | 8      | 8        | 7         | 5      | 4    |
| 12 | 29  | 5     | 29        | 5       | 8      | 8        | 7         | 5      | 4    |
| 13 | 29  | 5     | 5         | 29      | 8      | 8        | 7         | 5      | 4    |
| 14 | 25  | 0     | 0         | 0       | 75     | 0        | 0         | 0      | 0    |
| 15 | 30  | 1     | 1         | 1       | 1      | 64       | 1         | 1      | 0    |
| 16 | 29  | 3     | 3         | 3       | 4      | 4        | 49        | 3      | 2    |
| 17 | 30  | 6     | 6         | 6       | 8      | 8        | 7         | 25     | 4    |
| 18 | 29  | 7     | 7         | 7       | 10     | 10       | 8         | 7      | 16   |
| 19 | 5   | 29    | 29        | 5       | 8      | 8        | 7         | 5      | 4    |
| 20 | 5   | 29    | 5         | 29      | 8      | 8        | 7         | 5      | 4    |
| 21 | 0   | 25    | 0         | 0       | 75     | 0        | 0         | 0      | 0    |
| 22 | 1   | 30    | 1         | 1       | 1      | 64       | 1         | 1      | 0    |
| 23 | 3   | 29    | 3         | 3       | 4      | 4        | 49        | 3      | 2    |
| 24 | 6   | 30    | 6         | 6       | 8      | 8        | 7         | 25     | 4    |
| 25 | 7   | 29    | 7         | 7       | 10     | 10       | 8         | 7      | 16   |
| 26 | 5   | 5     | 29        | 29      | 8      | 8        | 7         | 5      | 4    |
| 27 | 0   | 0     | 25        | 0       | 75     | 0        | 0         | 0      | 0    |
| 28 | 1   | 1     | 30        | 1       | 1      | 64       | 1         | 1      | 0    |
| 29 | 3   | 3     | 29        | 3       | 4      | 4        | 49        | 3      | 2    |
| 30 | 6   | 6     | 30        | 6       | 8      | 8        | 7         | 25     | 4    |
| 31 | 7   | 7     | 29        | 7       | 10     | 10       | 8         | 7      | 16   |
| 32 | 0   | 0     | 0         | 25      | 75     | 0        | 0         | 0      | 0    |
| 33 | 1   | 1     | 1         | 30      | 1      | 64       | 1         | 1      | 0    |
| 34 | 3   | 3     | 3         | 29      | 4      | 4        | 49        | 3      | 2    |
| 35 | 6   | 6     | 6         | 30      | 8      | 8        | 7         | 25     | 4    |
| 36 | 7   | 7     | 7         | 29      | 10     | 10       | 8         | 7      | 16   |
| 37 | 0   | 0     | 0         | 0       | 58     | 42       | 0         | 0      | 0    |
| 38 | 0   | 0     | 0         | 0       | 64     | 0        | 36        | 0      | 0    |
| 39 | 0   | 0     | 0         | 0       | 78     | 0        | 0         | 22     | 0    |
| 40 | 0   | 0     | 0         | 0       | 85     | 0        | 0         | 0      | 15   |
| 41 | 0   | 0     | 0         | 0       | 0      | 57       | 43        | 0      | 0    |
| 42 | 1   | 1     | 1         | 1       | 2      | 66       | 2         | 25     | 1    |
| 43 | 2   | 2     | 2         | 2       | 4      | 66       | 3         | 2      | 16   |
| 44 | 3   | 3     | 3         | 3       | 5      | 5        | 51        | 25     | 2    |
| 45 | 4   | 4     | 4         | 4       | 6      | 6        | 51        | 4      | 16   |
| 46 | 7   | 7     | 7         | 7       | 11     | 11       | 9         | 25     | 16   |
| 47 | 10  | 10    | 10        | 10      | 15     | 15       | 13        | 10     | 7    |
| 48 | 5   | 5     | 5         | 5       | 10     | 10       | 8         | 5      | 50   | name, or names if a binary interaction term was included. The third column lists the coefficient for the corresponding term. The final column lists the standard deviation of the coefficient. The last row in each table is a standard error of estimation (SEE), which is the root mean square of the residuals between the NIR property and the interaction model estimate of the NIR property. Data presented in the first table for the RON model shows that two interaction terms were included in the equation: LSR*LtCat and Alkylate*Reformate. The large negative coefficient for the LSR*LtCat term indicates a strong negative interaction between these components, leading to a lower RON value than predicted by a linear model when these components are both present.

RON

| | | | |
|---|---|---|---|
| Raffinate | | 78.4194 | 0.21 |
| Naphtha | | 67.2022 | 0.21 |
| CatGas | | 89.3613 | 0.071 |
| Alkylate | | 95.6966 | 0.10 |
| Reformate | | 106.117 | 0.15 |
| MTBE | | 115.74 | 0.25 |
| LSR | | 82.1305 | 0.26 |
| LtCat | | 98.6244 | 0.27 |
| Butane | | 90.322 | 0.25 |
| LSR | LtCat | −50.2765 | 2.6 |
| Alkylate | Reformate | 5.9259 | 0.79 |
| SEE = 0.1539 | | | |

MON

| | | | |
|---|---|---|---|
| Raffinate | | 78.6548 | 0.0078 |
| Naphtha | | 68.2089 | 0.0077 |
| CatGas | | 79.3543 | 0.0031 |
| Alkylate | | 91.9911 | 0.0038 |
| Reformate | | 90.6469 | 0.0046 |
| MTBE | | 99.2755 | 0.013 |
| LSR | | 81.1189 | 0.0099 |
| LtCat | | 84.1161 | 0.012 |
| Butane | | 85.3005 | 0.011 |
| LSR | LtCat | −9.14628 | 0.097 |
| CatGas | Butane | −2.0136 | 0.042 |
| CatGas | LtCat | −1.67372 | 0.039 |
| Alkylate | MTBE | −2.1718 | 0.068 |
| SEE = 0.00574 | | | |

MTBE

| | | | |
|---|---|---|---|
| Raffinate | | −1.10448 | 0.073 |
| Naphtha | | −0.852028 | 0.073 |
| CatGas | | 0.155485 | 0.033 |
| Alkylate | | 0.36174 | 0.034 |
| Reformate | | 3.7531 | 0.061 |
| MTBE | | 102.834 | 0.22 |
| LSR | | −0.992607 | 0.11 |
| LtCat | | −1.02896 | 0.11 |
| Butane | | −5.6148 | 0.16 |
| CatGas | Butane | 6.33828 | 0.42 |
| MTBE | Butane | 30.9426 | 2.1 |
| Reformate | MTBE | −21.6292 | 0.93 |
| LSR | LtCat | −12.5354 | 0.91 |
| LSR | Butane | −12.0534 | 1.1 |
| MTBE | LtCat | 18.1851 | 1.7 |
| CatGas | Reformate | −3.75236 | 0.28 |
| CatGas | MTBE | −6.87382 | 0.58 |
| SEE = 0.0541 | | | |

AROMATICS

| | | | |
|---|---|---|---|
| Raffinate | | 5.75896 | 0.37 |
| Naphtha | | 11.4278 | 0.36 |
| CatGas | | 27.5412 | 0.13 |
| Alkylate | | −3.3166 | 0.21 |
| Reformate | | 79.3063 | 0.26 |
| MTBE | | 32.7096 | 0.61 |
| LSR | | 0.676109 | 0.46 |
| LtCat | | 20.4538 | 0.59 |
| Butane | | 7.3376 | 0.55 |
| LSR | LtCat | −71.1351 | 4.5 |
| Alkylate | LtCat | −11.6863 | 2.0 |
| Alkylate | Butane | −13.2422 | 2.2 |
| Reformate | MTBE | −19.9967 | 4.5 |
| SEE = 0.2696 | | | |

OLEFINS

| | | | |
|---|---|---|---|
| Raffinate | | 1.46585 | 1.3 |
| Naphtha | | 8.35263 | 1.3 |
| CatGas | | 19.2134 | 0.44 |
| Alkylate | | −2.33833 | 0.63 |
| Reformate | | −9.28298 | 0.90 |
| MTBE | | 8.81847 | 1.6 |
| LSR | | 5.28504 | 1.6 |
| LtCat | | 43.3112 | 1.7 |
| Butane | | 7.74533 | 1.5 |
| LSR | LtCat | −132.635 | 16 |
| Alkylate | Reformate | 20.8003 | 4.9 |
| SEE = 0.9521 | | | |

SATURATES

| | | | |
|---|---|---|---|
| Raffinate | | 92.2627 | 2.6 |
| Naphtha | | 79.3821 | 2.6 |
| CatGas | | 53.0801 | 0.89 |
| Alkylate | | 108.324 | 1.3 |
| Reformate | | 31.3031 | 1.8 |
| MTBE | | 57.6233 | 3.2 |
| LSR | | 95.6079 | 3.3 |
| LtCat | | 37.4076 | 3.4 |
| Butane | | 84.59 | 3.1 |
| LSR | LtCat | 183.138 | 32 |
| Alkylate | Reformate | −17.1948 | 9.9 |
| SEE = 1.923 | | | |

Gravity

| | | | |
|---|---|---|---|
| Raffinate | | 0.689587 | 2.5e-006 |
| Naphtha | | 0.755991 | 2.5e-006 |
| CatGas | | 0.746106 | 1.1e-006 |
| Alkylate | | 0.697167 | 1.4e-006 |
| Reformate | | 0.837497 | 2.1e-006 |
| MTBE | | 0.771515 | 7.1e-006 |
| LSR | | 0.637462 | 2.5e-006 |
| LtCat | | 0.650611 | 3.1e-006 |
| Butane | | 0.641433 | 3.9e-006 |
| Reformate | MTBE | −0.145052 | 0.000033 |
| CatGas | MTBE | −0.0732896 | 0.000020 |
| CatGas | Reformate | −0.0206071 | 9.6e-006 |
| Alkylate | Butane | −0.0402734 | 0.000015 |
| CatGas | LtCat | 0.0268915 | 0.000013 |
| Alkylate | MTBE | −0.0440069 | 0.000024 |
| SEE = 1.861e-006 | | | |

T_10

| | | | |
|---|---|---|---|
| Raffinate | | 141.263 | 8.6 |
| Naphtha | | 190.535 | 6.7 |
| CatGas | | 138.052 | 2.4 |
| Alkylate | | 162.901 | 3.0 |
| Reformate | | 161.388 | 4.0 |
| MTBE | | 129.268 | 8.2 |
| LSR | | 70.7753 | 8.7 |
| LtCat | | 67.2717 | 10. |
| Butane | | −71.0961 | 12 |
| LtCat | Butane | −117.565 | 96 |
| LSR | Butane | −124.739 | 95 |
| Raffinate | LtCat | −107.841 | 82 |
| SEE = 4.988 | | | |

T_50

| | | | |
|---|---|---|---|
| Raffinate | | 176.154 | 3.9 |
| Naphtha | | 244.42 | 3.8 |
| CatGas | | 230.636 | 1.8 |
| Alkylate | | 264.45 | 2.2 |
| Reformate | | 352.445 | 3.9 |
| MTBE | | 127.334 | 11 |
| LSR | | 70.7342 | 3.8 |
| LtCat | | 49.9196 | 6.1 |
| Butane | | 78.9705 | 5.7 |
| Alkylate | Reformate | −81.5301 | 15 |
| CatGas | Alkylate | −50.4229 | 13 |

-continued

| | | | |
|---|---|---|---|
| Alkylate | MTBE | −163.867 | 36 |
| Reformate | MTBE | −172.029 | 51 |
| CatGas | MTBE | −70.9913 | 31 |
| CatGas | LtCat | 59.0675 | 20. |
| CatGas | Butane | 39.9751 | 21 |
| Reformate | LtCat | 51.5132 | 29 |
| SEE = 2.826 | | | |
| T_90 | | | |
| Raffinate | | 329.732 | 6.8 |
| Naphtha | | 369.711 | 6.3 |
| CatGas | | 366.327 | 1.8 |
| Alkylate | | 301.017 | 3.4 |
| Reformate | | 328.979 | 5.3 |
| MTBE | | 297.301 | 10. |
| LSR | | 301.468 | 7.6 |
| LtCat | | 292.406 | 8.2 |
| Butane | | 303.325 | 9.7 |
| Alkylate | Reformate | 27.1067 | 20. |
| LSR | LtCat | 125.521 | 63 |
| Reformate | Butane | −91.0178 | 44 |
| Naphtha | Reformate | 69.7596 | 37 |
| Alkylate | Butane | −61.3559 | 32 |
| Raffinate | MTBE | 156.004 | 1.2e-002 |
| Alkylate | LtCat | −39.9282 | 27 |
| MTBE | LSR | 161.225 | 1.1e-002 |
| SEE = 3.695 | | | |
| VL | | | |
| Raffinate | | 156.953 | 8.9 |
| Naphtha | | 231.677 | 6.9 |
| CatGas | | 172.864 | 2.4 |
| Alkylate | | 184.935 | 3.1 |
| Reformate | | 213.813 | 4.2 |
| MTBE | | 97.1842 | 8.5 |
| LSR | | 61.9612 | 9.1 |
| LtCat | | 69.9724 | 11 |
| Butane | | −27.2399 | 12 |
| LtCat | Butane | −141.312 | 1.0e-002 |
| Raffinate | LtCat | −126.592 | 85 |
| LSR | Butane | −142.39 | 99 |
| SEE = 5.169 | | | |
| RVP | | | |
| Raffinate | | 9.12091 | 0.28 |
| Naphtha | | −0.224335 | 0.22 |
| CatGas | | 6.6828 | 0.075 |
| Alkylate | | 7.41011 | 0.12 |
| Reformate | | 5.95181 | 0.13 |
| MTBE | | 9.26014 | 0.27 |
| LSR | | 14.8045 | 0.29 |
| LtCat | | 18.647 | 0.28 |
| Butane | | 51.3745 | 0.33 |
| LSR | Butane | 31.377 | 3.1 |
| Alkylate | LtCat | −10.7497 | 1.2 |
| Raffinate | Alkylate | −6.6299 | 1.1 |
| SEE = 0.1616 | | | |
| BENZENE | | | |
| Raffinate | | −0.0127345 | 0.0023 |
| Naphtha | | 1.85664 | 0.0028 |
| CatGas | | 0.129872 | 0.00077 |
| Alkylate | | −0.047662 | 0.0013 |
| Reformate | | 0.273799 | 0.0013 |
| MTBE | | 0.245672 | 0.0028 |
| LSR | | −0.163949 | 0.0023 |
| LtCat | | −0.575439 | 0.0029 |
| Butane | | 0.105123 | 0.0027 |
| Alkylate | LtCat | 0.890009 | 0.012 |
| Naphtha | Alkylate | −0.830321 | 0.012 |
| SEE = 0.001678 | | | |

Figure 2:
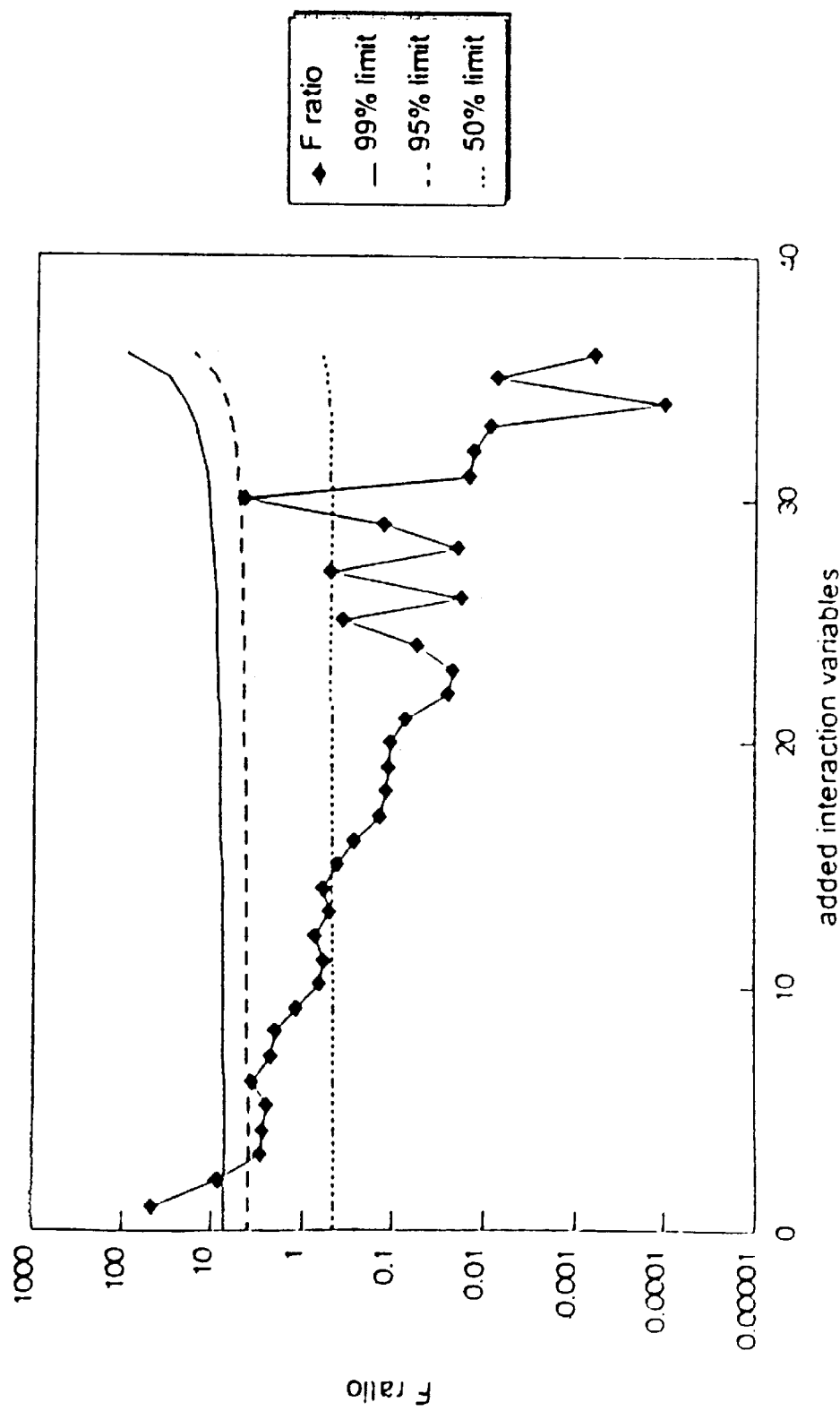
FIG. 2 is a graph showing the F test ratio resulting from each added binary interaction term in a model for prediction of RON.

FIG. 2 shows the F test ratios observed for each added binary interaction coefficient for RON, along with limit lines at 99%, 95% and 50% confidence levels. The first two binary interaction coefficients dare actually above the 99% confidence line, making it highly likely that these coefficients are contributing to accurate modeling of RON. After ten terms, the F ratio drops below the 50% limit for most of the added coefficients, showing that beyond ten terms, the equation is less accurate than random guessing, which indicates that there is information in the NIR RON measurement that the composition is incapable of modeling.

The preceding Example is intended to describe certain preferred embodiments of the present invention. It should be appreciated, however, that obvious additions and modifications to the invention will be apparent to one skilled in the art. The invention is not limited except as set forth in the claims.

What is claimed is:

1. A method for preparing a mixture comprising at least two components and having a value of an intrinsic property; said method comprising steps of:
   (a) selecting said components and an interaction model equation; wherein said interaction model equation relates amounts of the components to the intrinsic property of the mixture;
   (b) selecting experimental compositions, each of said experimental compositions comprising at least one of said components;
   (c) determining a correlational property of each of the experimental compositions by a correlational technique;
   (d) determining a set of coefficients for said equation; by testing the statistical significance of each possible interaction coefficient and retaining only those interaction coefficients that are statistically significant;
   (e) using said coefficients and said equation to predict concentrations of said components which will produce a desired value of said intrinsic property when said components are blended in said concentrations; and
   (f) blending said components in said concentrations.

2. The method of claim 1 in which said mixture is a liquid mixture.

3. The method of claim 2 in which said correlational technique is a spectroscopic technique.

4. The method of claim 3 in which said equation is an interaction model.

5. The method of claim 4 in which said spectroscopic technique is NIR spectroscopy.

6. The method of claim 5 in which there are at least five components.

7. The method of claim 6 in which said liquid mixture is a gasoline blend and an NIR correlational model is used to determine the correlational properties.

8. The method of claim 7 in which said intrinsic property is selected from the group consisting of RON, MON, (R+M)/2, T10, T50, T90, E200, E300, %Aromatics, %MTBE, %Benzene, RVP, V/L and specific gravity.

9. The method of claim 8 in which said interaction model is a binary interaction model.

10. An automated apparatus for producing mixtures of liquid components and analyzing said mixtures spectroscopically; said automated apparatus comprising:
   a) a plurality of reservoirs, each of said reservoirs capable of containing one of said liquid components;
   b) a plurality of pumps or valves, each of said pumps or valves associated with one of said reservoirs and capable of regulating flow from said one of said reservoirs;
   c) a mixing chamber capable of receiving flow from said reservoirs to produce a mixture of liquid components;
   d) a spectrophotometer capable of analyzing said mixture of liquid components to determine a correlational property; and
   e) a computer configured to control said spectrophotometer and said pumps or valves and to store and analyze data from said spectrophotometer by determining a set of coefficients for an interaction model equation relating amounts of components to an intrinsic mixture property by testing the statistical significance of each possible interaction coefficient and retaining only those interaction coefficients that are statistically significant.

11. The apparatus of claim 10 in which there are at least five components.

12. The apparatus of claim 11 in which said computer is programmed to perform an iterative optimization to determine optimum proportions of said components.

13. The apparatus of claim 12 in which said spectrophotometer is a NIR spectrophotometer.

14. The apparatus of claim 13 in which said components are gasoline blend stocks.

15. The apparatus of claim 11 in which said spectrophotometer is a NIR spectrophotometer.

16. The apparatus of claim 15 in which said components are gasoline blend stocks.

* * * * *